United States Patent [19]
Heumann et al.

[11] Patent Number: 5,727,919
[45] Date of Patent: Mar. 17, 1998

[54] AUTOMATIC BEVERAGE TERMINAL

[76] Inventors: Cordula Heumann; Friedrich Heumann, both of Paul-Schilder-Weg 19, D-90455 Nürnberg, Germany

[21] Appl. No.: 640,770

[22] PCT Filed: Sep. 1, 1995

[86] PCT No.: PCT/EP95/03449

§ 371 Date: May 7, 1996

§ 102(e) Date: May 7, 1996

[87] PCT Pub. No.: WO96/07993

PCT Pub. Date: Mar. 14, 1996

[30] Foreign Application Priority Data

Sep. 7, 1994 [DE] Germany ............ 44 31 870.7

[51] Int. Cl.⁶ .................................................. B65G 1/00
[52] U.S. Cl. ............... 414/268; 414/269; 414/786; 414/792.9; 414/928; 414/929
[58] Field of Search ...................... 414/792.9, 796.9, 414/928, 929, 268, 269, 273, 786

[56] References Cited

U.S. PATENT DOCUMENTS

| | | |
|---|---|---|
| 3,343,638 | 9/1967 | Putman . |
| 3,468,436 | 9/1969 | Manney et al. ............ 414/792.9 |
| 3,480,161 | 11/1969 | Bason ........................ 414/792.9 |
| 3,719,287 | 3/1973 | Noreen et al. . |
| 4,253,573 | 3/1981 | Dubberly et al. . |
| 4,358,236 | 11/1982 | Dudley ....................... 414/929 |
| 5,087,169 | 2/1992 | Tebke ........................ 414/796.9 |
| 5,098,254 | 3/1992 | Becicka et al. ............ 414/792.9 |
| 5,186,281 | 2/1993 | Jenkins . |
| 5,363,310 | 11/1994 | Haj-Ali-Ahmadi et al. ......... 414/273 |
| 5,582,497 | 12/1996 | Noguchi ..................... 414/268 |

FOREIGN PATENT DOCUMENTS

| | | |
|---|---|---|
| A 0 010 686 | 5/1980 | European Pat. Off. . |
| A 0 590 646 | 4/1994 | European Pat. Off. . |
| A 0 591 845 | 4/1994 | European Pat. Off. . |
| A 2 540 080 | 8/1984 | France . |
| A 2 694 487 | 2/1994 | France . |
| 3301905 | 7/1984 | Germany . |
| 244 099 A1 | 3/1987 | Germany . |
| U 94 03 105 | 7/1994 | Germany . |
| 903 228 | 8/1962 | United Kingdom . |
| WO A 87 01102 | 2/1987 | WIPO . |

OTHER PUBLICATIONS

CH-Z transport, forder- und lagertechnik 1983, issue 6, pp. 19-20.

*Primary Examiner*—Karen B. Merritt
*Assistant Examiner*—Douglas Hess
*Attorney, Agent, or Firm*—Knobbe, Martens, Olson & Bear, LLP

[57] ABSTRACT

A beverage terminal for the automatic delivery of beverage crates including a delivery terminal for pallets charged with beverage crates, at least one high-shelf, an individualizing device, at least one depot, at least one customer conveyor, and at least one beverage supply point provided with a customer control panel. The individualizing device and a depalletizer include at least one horizontally arranged linear conveyor assigned to a storage surface of the depot. The linear conveyor has a gripping mechanism for gripping and lifting or lowering individual beverage crates.

22 Claims, 5 Drawing Sheets

AUTOMATIC BEVERAGE TERMINAL

BACKGROUND OF THE INVENTION

The invention relates to a beverage terminal for the automatic supply of beverage crates.

1. Field of the Invention

The well-known selling places for beverage crates substantially are formed by so-called self-service markets where a customer must transport beverage crates to a pay desk within the market and after having paid must take them to his vehicle. The return of the empties takes place in a similar manner, usually they are to be delivered to a pay desk separately. It is disadvantageous that the entire purchase step is expensive in time and arduous for the customer and that such a beverage market requires a large surface as also sufficient passageways for the customers must be available. There is also required a large number of employees for refilling the beverage crates, for performing the payment step and for attending to the customers.

2. Description of the Related Art

It is a further disadvantage of well-known self-service markets that they are subject to the law relating to the closing time of shops, so that the customer can only do his shopping during a few hours of the day.

German Patent DE-PS 33 01 905 relates to an automatic machine for selling goods charging the money by itself, in which individual bottles placed on inclined storages of filled goods can selectively be transported to a supply area by means of a transverse conveyor. In addition to the supply area there is provided an area for receiving empties where empties can be placed on inclined belts for storing empties, by using the transverse conveyor. This goods automate is able to deliver or receive individual bottles of beverages.

There is neither provided a fully automated course of operation nor is it possible with this construction to handle or even discharge from and/or stack on pallets larger units of e.g. beverage crates.

The article in the Journal "Transport-, Förder- und Lagertechnik, 1984, vol. 4, pages 9 to 12" describes a distribution center for books, wherein arriving pallets are placed in a high-shelf storage. From said high-shelf storage the pallets are either distributed in the shop or packed in partial quantities and transferred to an intermediate storage. This is followed by a consignment stock where individual books are stored temporarily for subsequent packing and commissioning. The entire storage system is controlled by a computer.

The closest prior art is known from EP-A2-590 646 and DE-OS 42 32 833. In these previously known automatic beverage terminals the intermediate stocking of the beverage crates takes place in a depot which is formed either by inclined raceways or by turning-around storages. With inclined race-ways there can arise the problem that individual beverage crates are blocked by pieces of glass, decontaminations or the like or by tilting or getting out of place of the crates themselves. Depending on the respective conditions of use and the storing capacity of the depot a turning-around storage can require a too long access period.

The invention is based on the problem to provide a beverage terminal for the automatic supply of beverage crates, offering to the customer a large number of different beverages in a fully automatical mode of operation and without personnel being required, in a safe and quick mode of working, and distinguishing by very short access periods to the depot.

SUMMARY OF THE INVENTION

According to the invention the problem is solved by the features of the main claim, the subclaims comprising advantageous embodiments of the invention.

The beverage terminal according to the invention thus allows to sell to a customer sets of beverage containers in an automated manner, said sets of containers consisting either of beverage crates or of one-way containers. The beverage crates usually contain reusable bottles that are supplied together with the beverage crates against payment of a respective deposit and are taken back with the deposit being returned. One-way container sets are not taken back, these are rather disposed of separately. The beverage terminal can be adapted to the respective construction of the beverage crates or the containers. In the present invention the term beverage crates comprises both, namely beverage crates containing reusable bottles and sets with one-way bottles, cans, plastic wrappings, or the like.

According to a preferred embodiment of the invention there is provided an empties receiving point as well as corresponding storage places for empties and depalletizing means for adapting the beverage terminal to reusable beverage crates and reusable bottles. These pieces of equipment can be dispensed with if one-way containers are being used.

The following is based on an embodiment of the invention where beverage crates with reusable bottles are used. It is preferred that such a beverage terminal exhibits the following basic unit assembly groups: A supply terminal for the delivery of pallets charged with beverage crates, at least one high-shelf vehicle serving for the stockpiling of pallets in a high-shelf, an individualizing means for individualizing the beverage crates, at least one depot wherein the individual beverage crates are stored, at least one boxtype customer vehicle or a customer conveyor means for taking the crates from the depot and for transporting the crates to a beverage supply point which is provided with a customer control panel. According to the invention it is also provided that the individualizing means and the depalletizing means comprise at least one horizontal linear conveyor which is assigned to a storage surface of the depot and which is provided with gripping means for gripping and lifting/lowering individual beverage crates.

The beverage terminal according to the invention distinguishes by a number of considerable advantages. The substantial advantage resides in the fact that the beverage terminal does not require any personnel for operation thus considerably reducing the operating costs. Furthermore there is only required a very small space as no passageways for customers are required. From the fully automatical control there result very short access times, thus enabling the customer to receive the desired beverage crates in a much shorter period of time. As the entire operation of the beverage terminal takes place in a fully automated manner, the entire execution, refilling and stock-keeping can be optimized, too.

The beverage terminal according to the invention is an entirely novel technical system, which did not exist in a similar manner so far. This particularly results from the large weight of the beverage crates, from the fragility of the bottles and from the problem of an appropriate handling of the beverage crates. It is admitted that in the field of storage technology the most different partial components are known, however, these were never before combined to a functioning overall system; this can also be gathered from the cited references. In addition to the requirements to be met by the stock-keeping and automatic control technology, a beverage terminal incurs further problems which were solved by the invention for the first time. For instance, the customer's conduct is to be considered. The customer needs not wait for extended periods of time, he will not be prepared to wait several minutes for the delivery of the goods. Accordingly, the beverage terminal must be construed such that very short access times result. In addition, a customer will not be prepared to accept alternative products if the desired product is not available. For this reason the stock of a beverage terminal must be sufficient and reusable automatically in a manner that the supply of the customers is guaranteed also in rush hours. A further problem arises from the taking back of empties. As this is mandatorily required for ecological reasons, the beverage terminal must comprise two complete storage areas, namely one storage area for full beverage containers and one storage area for empties. The two areas must be connected to result in a safely functioning course of operation.

It is preferred that the customer control panel is equipped with a card-reading means for cashless payment, enabling the customer to use his EC-card for completing the purchase. The secret number to be typed in guarantees a high degree of safety in operation. As EC-cards are not handed out to juveniles this also ensures that no juveniles or children can buy alcoholic drinks. In order to allow a problem-free return of empties it is preferred that an empties-reception point is assigned to the customer control panel which is connected with an empties storage place. Subsequent to the latter depalletizing means can be arranged for stacking the empty crates on pallets and for automatically transporting same.

In order to automate the entire delivery step it may be favorable to provide a reading means for identifying the delivered palletized beverage crates in the area of the delivery terminal. This allows to furnish the beverage terminal with full pallets by means of lorries, each of which is loaded with one kind of beverage crates. The truck driver will unload a full pallet by means of a fork lift and drive it to the delivery terminal. By means of a bar-code reading means the kind of beverage is defined there. If problems arise the driver can identify the kind of beverage by means of a hand scanner. From the delivery terminal the loaded pallet is placed in the high-shelf storage according to a chaotic storage system. In a similar manner, an empty pallet or a pallet charged with crates filled with empties can be taken from the high-shelf storage or it can be brought to the delivery terminal, so that the driver can transport the empties or the empty pallet away.

The described way of delivery can be performed at differently constructed delivery terminals. For instance, it is possible to equip the delivery terminal with a freight elevator in a manner that several operating levels of the beverage terminal can be used.

Controlled by a central processing unit the delivery terminal can also be served in a manner that without the return of pallets charged with empties or empty pallets merely a filling with full or empty pallets is possible, e.g. for starting up the beverage terminal. Individual, selectable pallets can also be channelled out, e.g. pallets with empty or full goods, respectively, or empty pallets, e.g. for emptying the beverage terminal or for removing specific beverage pallets, e.g. when the "used best before"-date has expired.

For supervising the delivery or the transporting away of pallets charged with empties it may be favorable to provide a delivery ticket printer in the area of the delivery terminal which will automatically issue a delivery ticket to the driver.

The individualizing means provided between the high-shelf storage and the depot favorably also comprises a depalletizing means as well as at least one individualizing vehicle which takes individual beverage crates from the depalletizing means and transports same to the depot.

According to the invention, the individual crates of the individualizing means are passed to the depot by means of conveyors driven by force.

Due to the use of the linear conveyor provided according to the invention it is possible to place the individual beverage crates on a horizontal storing surface of the depot. This intermediate storing in the depot can be performed according to a chaotic storing system, thus utilizing the overall surface of the depot in an optimal manner. As the beverage crates can be placed side by side as well as one on top of the other, it is possible to deposit the individual kinds of beverages in a manner matching the existing stock and the throughput amounts. As the linear conveyor, which is formed as a linear robot, thus has a direct access to the desired beverage crate very short access times result. The access ways can also be optimized, e.g. by appropriately placing frequently required kinds of beverages in areas favorable from an operational point of view of the linear conveyor.

One favorable development of the invention provides that the linear conveyor comprises a horizontal rail which is displaced on braces at a certain distance to the storing surface. When putting the rail higher there results a large vertical storage volume. As the linear conveyor overlaps the depot surface, the surface can be occupied in optimal manner by beverage crates, with no passageways etc. having to be kept free.

It is also favorable that a vehicle carrying said gripping means can be moved on the rail. To said vehicle a cross beam can be mounted which extends transversely with respect to the rail and which is displaceable in its longitudinal direction relative to the vehicle. This considerably extends the lateral action radius of the linear conveyor thus increasing the storage volume of the depot. Of course, it is also possible to mount the cross beam at two rails arranged in parallel to each other.

For facilitating the palletizing and/or depalletizing of the pallets by means of the linear conveyor and in order to treat the beverage crates to be transported to the customer terminal safely, it is favorable that the linear conveyor grips around conveyors which are assigned to the individualizing means, the customer conveyor means and/or the depalletizing means. Thus the linear conveyor can take beverage crates directly from said conveyors or place same thereon. In addition, the linear conveyor can either deliver said beverage crates directly from one conveyor to the other or deposit them in or take them from the depot.

It is preferred that the gripping means is designed such that it can be lowered vertically onto the upper edge area of the beverage crate and driven therefrom in upward direction. The gripping means, which may be provided with coupling means for gripping the beverage crate in detachable manner, thus can selectively lift or put down the beverage crate, independently from the number or the state of filling of the bottles contained in the beverage crate. Thus beverage crates with filled bottles as well as beverage crates with empties or empty crates can be handled safely in equal manner.

By means of a control and processing unit, which controls the linear conveyor, it is possible to memorize the respective storage position of a beverage crate and to find said crate again. For this purpose the crate can be provided with suitable data carriers, e.g. bar codes or the like, for identifying its content. There can also be provided means for differentiating kind and size of the beverage crate, e.g. crates for beer, water, divisionable special crates or crates in special sizes.

The box-type customer vehicle can be designed to take up several beverage crates for reducing the required driving distances.

BRIEF DESCRIPTION OF THE DRAWINGS

In the following the invention is described by means of an example with reference to the drawing.

In the drawings, identical parts are designated with identical reference numerals.

DESCRIPTION OF THE PREFERRED EMBODIMENTS

In the following example there is described a beverage terminal which is used for reusable bottles and/or reusable crates. However, the invention is net restricted to this embodiment, within the frame of this invention it is rather just as well possible to dispense with the empties-receiving unit and the assigned means, in particular the storage for the empties and the depalletizing means.

Figure 1:
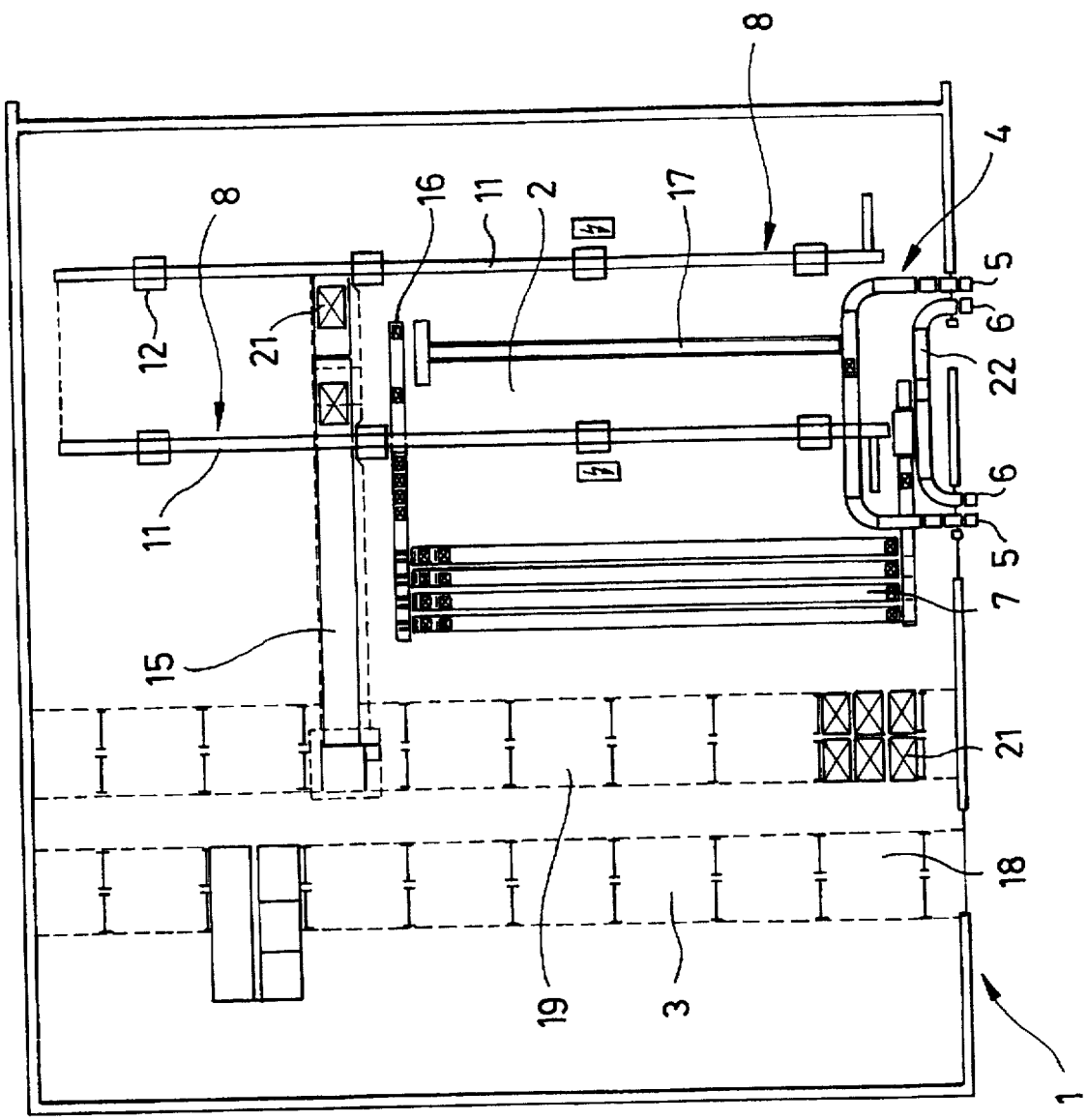
FIG. 1 shows a schematical illustration of a top view of the embodiment of the beverage terminal according to the invention.

FIG. 1 shows a top view of the construction of an embodiment of the beverage terminal according to the invention. In comprises a delivery terminal 1, which for instance can also be arranged in a different level. Thus pallets can be transported to a truck and/or be taken therefrom. The delivery terminal 1 comprises two raceways 18, 19 arranged in parallel to each other, one raceway for delivering pallets, the other raceway for supplying pallets to a not shown delivery vehicle. Both raceways 18 and 19 can be reached by a high-shelf vehicle that can be moved on rails within a high-shelf 3.

Figure 2:
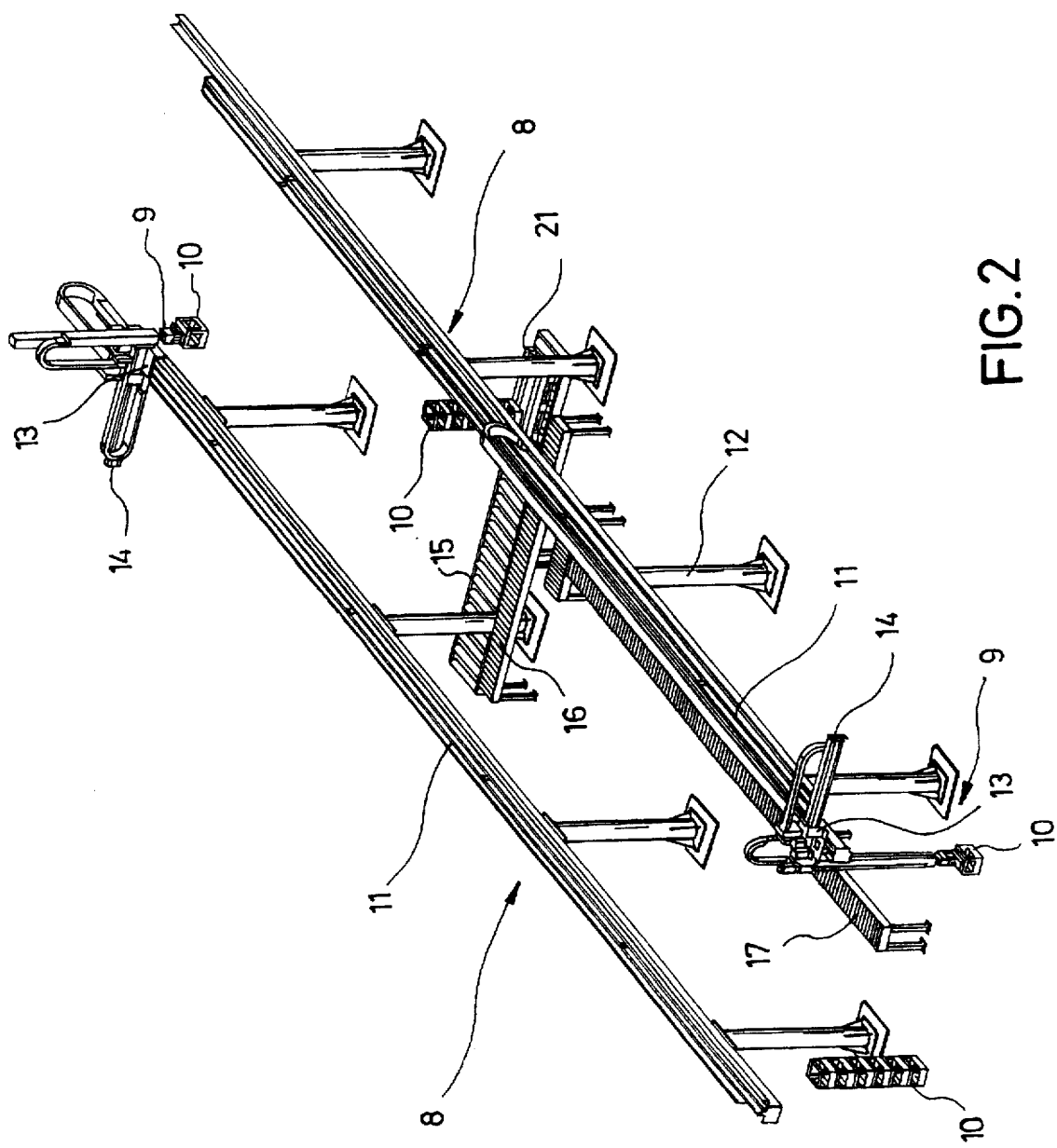
FIG. 2 shows a simplified perspective illustration of the depot with the linear conveyor.

The palletizing and/or depalletizing of the pallets is performed within the region of two linear conveyors 8 which are arranged in parallel to each other. Said conveyors comprise rails 11 mounted on braces 12 and extending in linear direction. As shown in FIG. 2, a vehicle 13 runs on rail 11, said vehicle carrying a cross beam 14. At said cross beam 14 gripping means 9 are provided for selectively gripping a beverage crate 10.

By means of linear conveyor 8 it is possible to grip a beverage crate, to displace same in a lifted state and to put it down at a predetermined position. The beverage crates can be placed side by side or in a stack one on top of the other.

The depalletizing of pallets 21, which are shown only in a schematical view, is performed in the following manner:

The pallets charged with beverage crates (see also FIG. 2) are transported from the high-shelf storage 3 to the working area of linear conveyor 8 by means of conveyor 15. There they are accessible for gripping means 9. Then individual crates are taken from pallet 21 one after the other and placed on the floor of depot 2.

The empty pallets 21 can be transported back to the high-shelf storage 3 via conveyor 15. However, it is also possible to stack empties which meanwhile accumulated in a storage for empties 7 and which was transported to the working area of the linear conveyor 8 via a conveyor 16 onto an empty pallet 21.

The storage for empties 7 comprises several conveyors arranged in parallel to each other. This allows to store the individual different crates with empties separately in an intermediate storage.

FIG. 1 also shows that a further conveyor 17 is arranged between the linear conveyors 8, said conveyor 17 being connected with a customer conveyor means 4. Said customer conveyor means 4 terminates in a beverage supply point 5 of a customer control panel. Thus the beverage crates placed on the conveyor belt or the conveyor 17 can be transported to the customer supply point 5 via customer conveyor means 4.

The conveyors 15, 16, 17 can be designed as conveyor belts, as raceways or the like. The same is true for customer conveyor means 4.

In the area of the customer control panel there is also provided an empties receiving point 6 which is connected to the storage for empties 7 via an empties conveyor 22. Thus, after having been identified and checked, the empties returned by the customer can be transported to the storage for empties 7.

FIG. 2 shows a perspective view of the construction of depot 2 according to the invention and particularly illustrates the working area of the linear conveyors 8 as well as conveyors 15, 16 and 17 assigned thereto.

Figure 3:
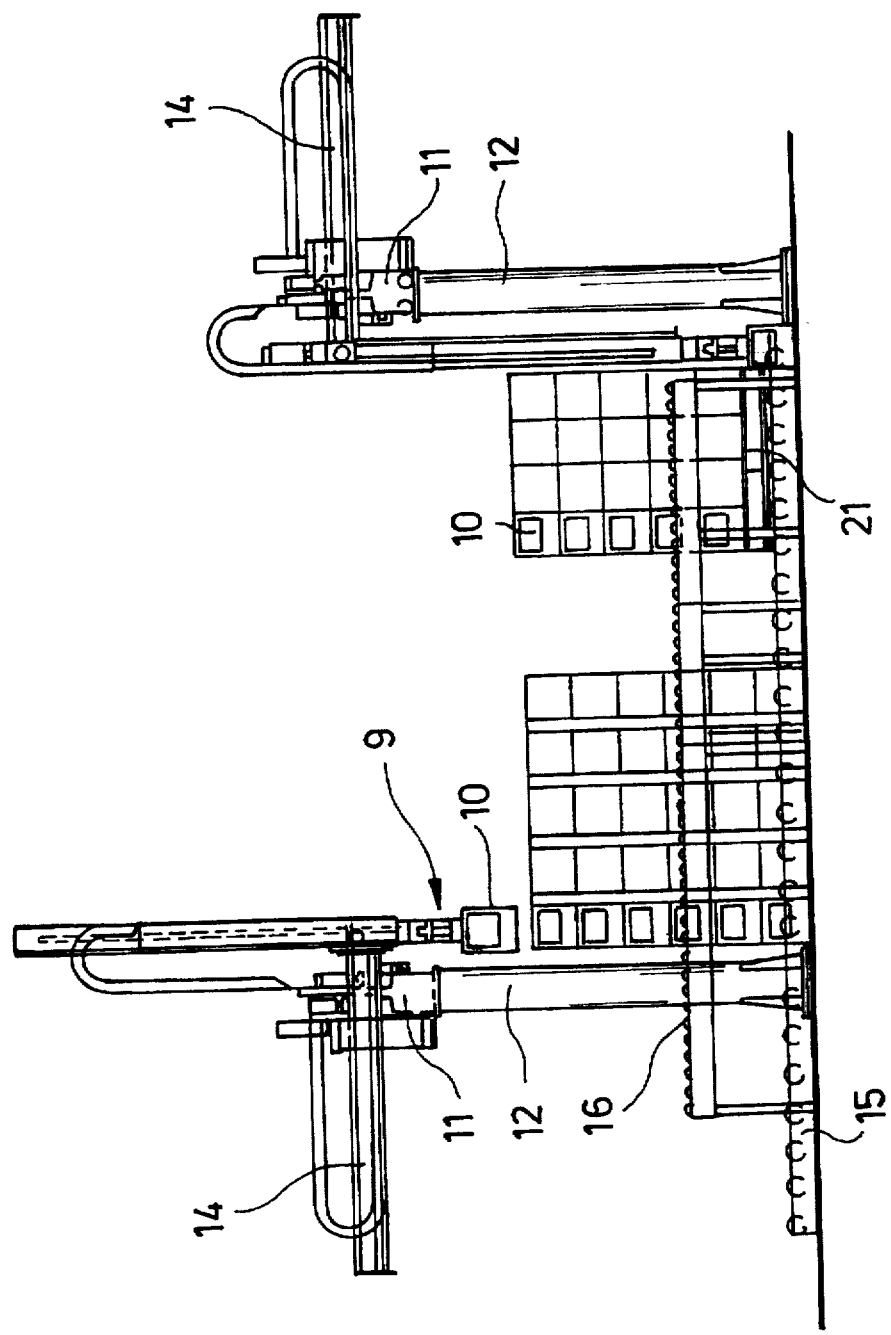
FIG. 3 shows a side view of the depot with the linear conveyor.

FIG. 3 is a side view of the depot shown in FIG. 2.

In the depot (buffer storage) 5 crates of one kind of beverage can be stacked one on top of the other. This allows to achieve a capacity of 2.200 crates. The arranging pattern, according to which the individual crates are deposited can be predetermined in dependency of the respective amount sold. Of course, the arranging pattern can vary constantly which is common use in a chaotic storage system, in order to adapt the depot to the respective conditions of use.

Figure 4:
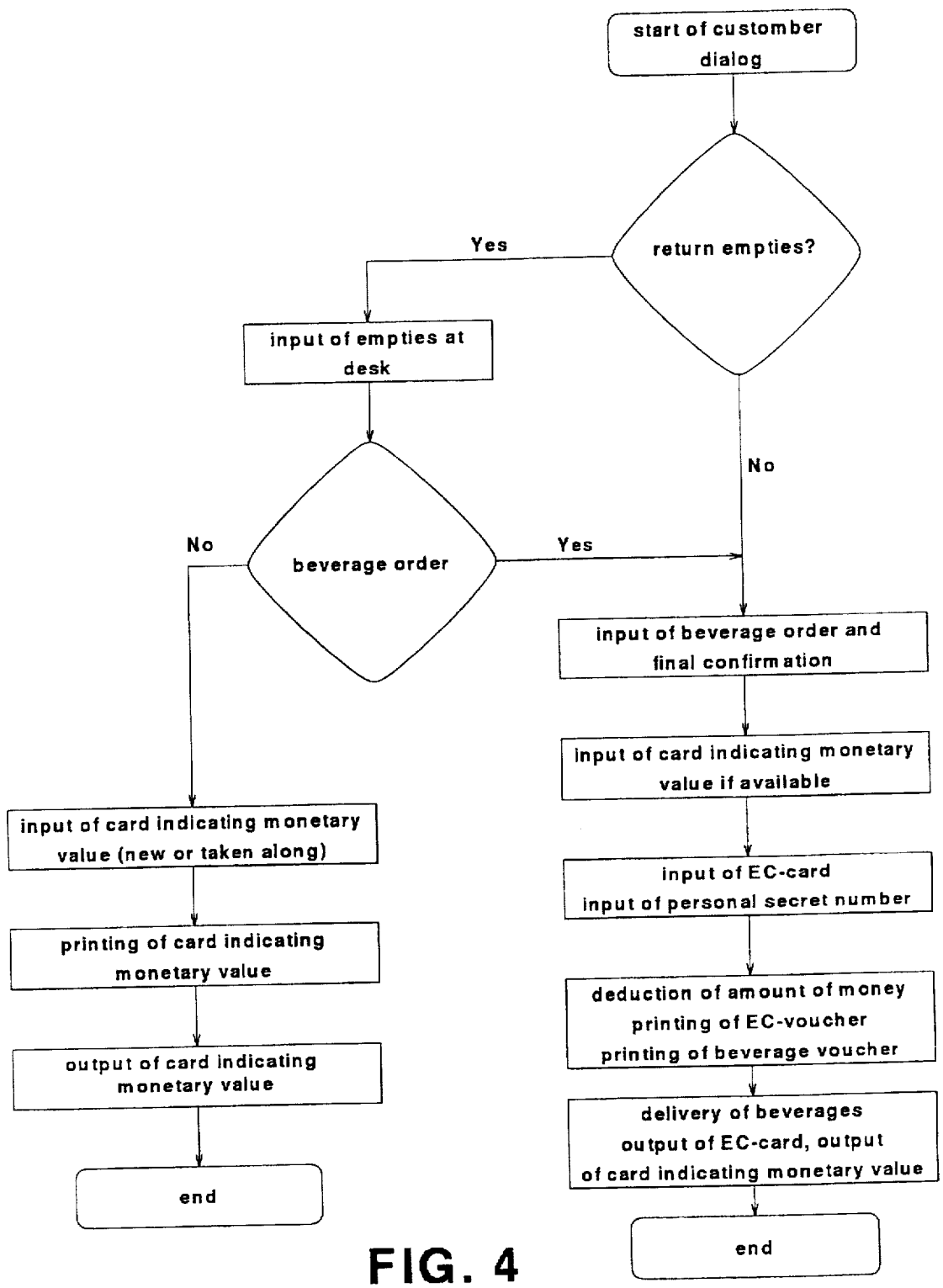
FIG. 4 shows a flow chart representing the course of the operating procedure to be performed by the customer at a customer control panel.
Figure 5:
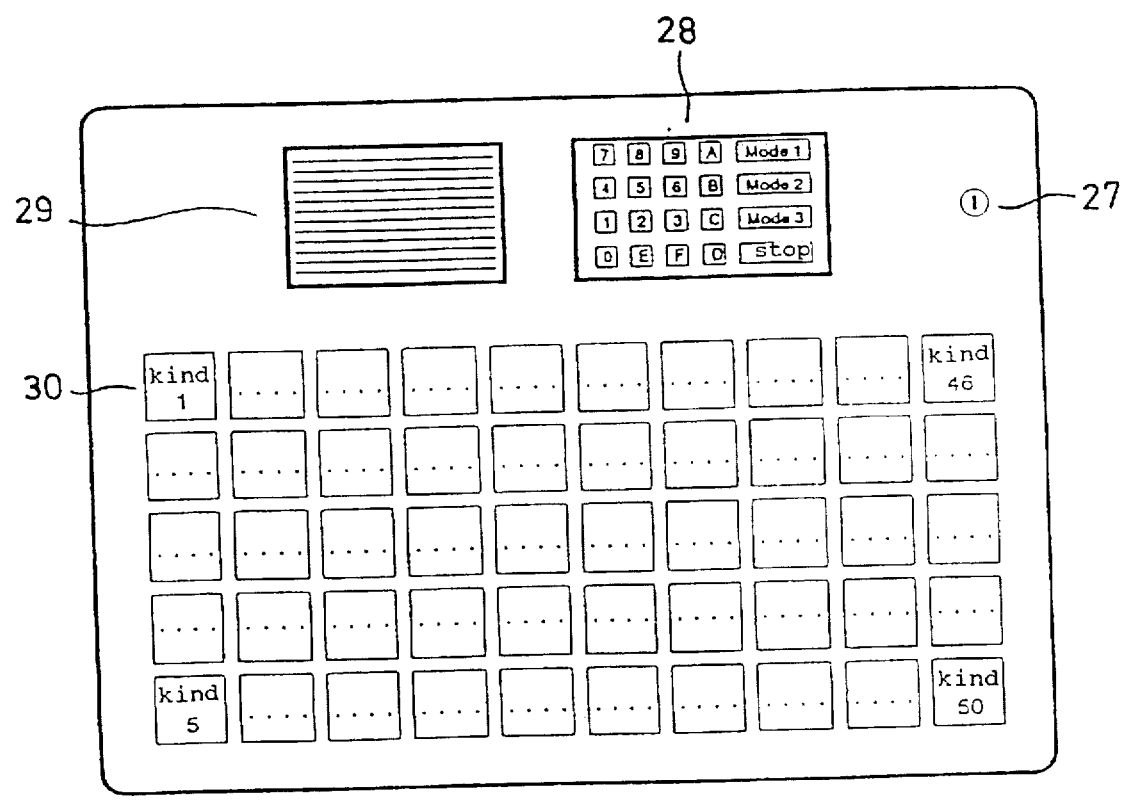
FIG. 5 shows a view of a customer control panel.

FIG. 5 illustrates a view of part of the customer control panel 7. Said control panel 7 comprises a key switch 27 by means of which the operators can perform manual functions. FIG. 5 neither illustrates the input for an EC-card nor the output of a card indicating the monetary value to be refunded for the returned empties. At the customer control panel there are provided functional keys 28, e.g. for typing in the secret number of the EC-card and for selecting the modes of operation. At first a customer will be asked at a display whether he wishes to return empties, as shown in FIG. 4. If this is affirmed the empties are to be inserted into the empties receiving point 6 and will be checked there automatically. It is determined whether the crates with the empties can be accepted and the filling state with empty bottles is being checked. If necessary, not accepted empties are returned to the customer. If a purchase is effected immediately thereafter, the value of the empties can be offset therewith immediately, it is also possible to issue a paper indicating the monetary value of the empties with the amount to be accounted or to be paid to the customer. When the customer selects the operation mode "beverage order" he can order the desired kind of beverage by means of beverage selection keys 30. In case the customer has a credit card or the like he can insert same for balancing. After the desired beverage crates were taken from depot 2 and transported to the beverage supply point 5, the required amount of money is automatically deducted from the EC-card, and the customer will obtain a voucher printed by a not shown printer. From this description it is obvious that the entire functional operation takes place automatically and that no cash transfer takes place. This increases the safety in operation. The danger of raids and burglaries is removed as there is no cash available.

By means of a central processing unit the individual functions of the beverage terminal are monitored, inter alia there is ascertained the filling state of the high-shelf storage and of the depot, in order to be able to make supplementary orders in time. This is all done automatically, just like the control optimizing the ways of all vehicles in order to realize the shortest possible access time. Of course, functions for emergency cases are provided, e.g. for clearing the beverage terminal or for influencing or bridging specific functions.

In summary the following must be stated:

The invention relates to a beverage terminal for the automatic supply of beverage crates comprising a delivery terminal 1 for pallets charged with beverage crates, at least one high-shelf 3, individualizing means, at least one depot 2, at least one customer conveyor means 4, at least one beverage supply point 5 provided with a customer control panel, characterized in that the individualizing means and the depalletizing means comprise at least one horizontally arranged linear conveyor 8 which is assigned to a storing surface of the depot 2 and which is provided with gripping means 9 for gripping and lifting/lowering individual beverage crates 10 (FIG. 2).

What is claimed is:

1. A beverage terminal for the automatic delivery of beverage crates, comprising:
   a delivery terminal for receiving from an external source, pallets charged with beverage crates;
   at least one high-shelf and an associated transport vehicle for transporting said pallets from said delivery terminal and stockpiling them on said high-shelf;
   a first conveyor for transporting said stockpiled pallets to a depalletizing location;
   a first gripper located above said first conveyor and movable in at least two axes for gripping and lifting crates of beverages from said pallets on said first conveyor;
   at least one depot for receiving crates of beverages lifted by said gripper from said first conveyor for temporary storage;
   at least one customer conveyor for transporting beverage crates from said depot to at least one beverage supply point provided with a customer control panel, wherein customers can purchase crates of beverages by operating said customer control panel at said beverage supply point; and
   a gripper comprising one of said first gripper or a second gripper that is also located above said first conveyor and moveable in at least two axes, for gripping and lifting beverage crates from said depot to said customer conveyor.

2. A beverage terminal according to claim 1, further including an empties receiving point assigned to said customer control panel, a storage for empties chargeable by means of said customer conveyor, and at least one of said grippers following the storage for empties and being connected with said high-shelf.

3. A beverage terminal according to claim 2, wherein at least one of said grippers comprises at least one horizontally arranged linear conveyor assigned to a storage surface of said depot, wherein said linear conveyor comprises a horizontal rail which is mounted on braces at a distance to the storage surface.

4. A beverage terminal according to claim 3, wherein a vehicle is movable on said horizontal rail and carries one of said grippers.

5. A beverage terminal according to claim 4, wherein at said vehicle a cross beam is mounted, extending in transverse direction to said rail and carrying one of said grippers.

6. A beverage terminal according to claim 5, wherein said cross beam is movable in its longitudinal direction relative to said vehicle.

7. A beverage terminal according to claim 3, wherein said linear conveyor traverses over a plurality of secondary conveyors provided for transporting full or empty pallets of beverage crates, and full or empty crates of beverages to and from a customer delivery point.

8. A beverage terminal according to claim 3, wherein said gripper can be lowered in vertical direction to an upper edge area of said beverage crate and can be driven therefrom in an upward direction.

9. A beverage terminal according to claim 8, wherein at least one of said grippers is provided with coupling means for detachably gripping said beverage crate.

10. A beverage terminal according to claim 3, wherein said linear conveyor comprises a driving means with a control and processing unit.

11. A beverage terminal according to claim 10, wherein said control and processing unit is designed to deliver and take up beverage crates that can be arranged side by side and/or one on top of the other.

12. An automated retail beverage terminal having a chaotic storage and retrieval capacity and a rapid response to customer orders, comprising:
    a terminal for receiving pallets loaded with beverage crates;
    a storage shelf;
    a transport vehicle for transporting said loaded pallets from said terminal to said storage shelf;
    a first conveyor for transporting said loaded pallets from said storage shelf to a depalletizing location;
    a second conveyor disposed above said depalletizing location;
    a vehicle moveable on said second conveyor having a gripper for gripping crates from said loaded pallets and transporting them to temporary storage locations on a floor of said terminal in a chaotic storage arrangement;
    a customer ordering location having a computer in communication with a control panel associated with the customer ordering location, the computer storing the location of said chaotically stored items; and
    a third conveyor for transporting crates of beverages selected by said gripper based on commands from said control panel from said depot floor to said customer ordering location.

13. The terminal of claim 12, wherein said second and third conveyors are oriented generally in parallel and said first conveyor is oriented transverse thereto, said gripper thus being movable over both said second and third conveyors.

14. The terminal of claim 12, wherein said computer further comprises a computer control means responsive to customer orders from said control panel to control the movement of said gripper, said vehicle, and said second and third conveyors to transport beverage crates from said first conveyor or said temporary storage locations to said customer ordering location.

15. A method of chaotic storage and retrieval in an automated retail beverage terminal enabling rapid response to customer orders, comprising the steps of:

receiving a pallet loaded with beverage crates from a terminal;

lifting a crate from said loaded pallet with a gripper mounted on a vehicle movable along a first conveyor disposed above said pallet and transporting said crate with said gripper to a temporary storage location on a floor of said terminal in a chaotic storage arrangement and storing information on the location of said crate in memory accessible by a computer;

selecting said crate stored at said temporary storage locations based on commands from a control panel mounted at a customer ordering location with the control panel being in communication with said computer; and in response to a customer request for said crate, using said information to locate said crate and lifting said selected crate with said gripper and transporting it to said customer ordering location along a second conveyor.

16. A method as defined in claim 15, comprising the further step of using said control panel to perform financial transactions relating to the payment for said crate.

17. A beverage terminal for the automatic delivery of beverage crates, comprising:

a delivery terminal for receiving, from an external source, pallets charged with beverage crates;

at least one high-shelf and an associated transport vehicle for transporting said pallets from said delivery terminal and stockpiling them on said high-shelf;

a first conveyor for transporting said stockpiled pallets to a depalletizing location;

a gripper located above said first conveyor and movable in at least two axes for gripping and lifting crates of beverages from said pallets on said first conveyor, said gripper comprising at least one horizontally arranged linear conveyor assigned to a storage surface of a depot, said linear conveyor comprising a horizontal rail which is mounted at a distance to the storage surface, and a vehicle movable on said horizontal rail, said vehicle having mounted thereto a cross beam extending in transverse direction to said rail and carrying said gripper, said cross beam being movable in its longitudinal direction relative to said vehicle;

said depot for receiving crates of beverages lifted by said gripper from said first conveyor for temporary storage;

at least one customer conveyor for transporting beverage crates from said depot to at least one beverage supply point provided with a customer control panel, wherein customers can purchase crates of beverages by operating said customer control panel at said beverage supply point.

18. A beverage terminal for the automatic delivery of beverage crates, comprising:

a delivery terminal for receiving, from an external source, pallets charged with beverage crates;

at least one high-shelf and an associated transport vehicle for transporting said pallets from said delivery terminal and stockpiling them on said high-shelf;

a first conveyor for transporting said stockpiled pallets to a depalletizing location;

a gripper located above said first conveyor and movable in at least two axes for gripping and lifting crates of beverages from said pallets on said first conveyor, said gripper comprising at least one horizontally arranged linear conveyor assigned to a storage surface of a depot, said linear conveyor comprising a horizontal rail which is mounted on braces at a distance to the storage surface, and said linear conveyor traversing over a plurality of secondary conveyors provided for transporting full or empty pallets of beverage crates, and full or empty crates of beverages to and from a customer delivery point;

said depot for receiving crates of beverages lifted by said gripper from said first conveyor for temporary storage;

at least one customer conveyor for transporting beverage crates from said depot to at least one beverage supply point provided with a customer control panel, wherein customers can purchase crates of beverages by operating said customer control panel at said beverage supply point.

19. A beverage terminal for the automatic delivery of beverage crates, comprising:

a first gripper movable in at least two axes for gripping and lifting crates of beverages from pallets;

at least one depot for receiving crates of beverages lifted by said gripper for temporary storage;

at least one customer conveyor for transporting beverage crates from said depot to at least one beverage supply point provided with a customer control panel, wherein customers can purchase crates of beverages by operating said customer control panel at said beverage supply point; and a gripper comprising one of said first gripper or a second gripper that is moveable in at least two axes, for gripping and lifting beverage crates from said depot to said customer conveyor.

20. A beverage terminal according to claim 19, further comprising a delivery terminal for receiving from an external source pallets charged with beverage crates;

at least one high-shelf and an associated transport vehicle for transporting said pallets from said delivery terminal and stockpiling them on said high-shelf;

a pallet conveyor positioned below said first and second grippers for transporting said stockpiled pallets to a depalletizing location.

21. A system for controlling the delivery of goods and accepting the return of empties, comprising:

a customer control panel for communication with a customer, whereby said customer control panel has functional keys and a card reader that are in communication with a computer so a customer can order goods;

a supply point adjacent the customer control panel for supplying the goods to the customer;

a customer conveyor for delivering the goods to the supply point;

a gripper in communication with the computer for depositing goods from a supply source to a depot and moving the goods ordered by the customer from the depot to the customer conveyor as directed by the computer;

an empties receiving point adjacent the customer control panel for receiving empties;

an empties conveyor for receiving the empties from the empties receiving point and delivering the empties to an empties storage.

22. A system as defined in claim 21, wherein the gripper deposits the goods to a location in a chaotic manner with the computer tracking the location and directing the gripper to that location when the goods at that location are moved to the customer conveyor.

* * * * *